United States Patent
Oh et al.

(10) Patent No.: US 8,055,319 B2
(45) Date of Patent: Nov. 8, 2011

(54) SENSOR FOR MEASURING LIVING BODY INFORMATION AND EARPHONE HAVING THE SAME

(75) Inventors: Jung-Taek Oh, Yongin-si (KR);
Sun-Tae Jung, Yongin-si (KR);
Dong-Kyoon Han, Seongnam-si (KR);
Jae-Geol Cho, Yongin-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 527 days.

(21) Appl. No.: 12/198,162

(22) Filed: Aug. 26, 2008

(65) Prior Publication Data
US 2009/0062661 A1  Mar. 5, 2009

(30) Foreign Application Priority Data
Aug. 27, 2007 (KR) .................. 10-2007-0086098

(51) Int. Cl.
*A61B 5/00* (2006.01)
(52) U.S. Cl. ........ 600/310; 600/340; 600/407; 600/473; 600/476; 356/432

(58) Field of Classification Search .................. 600/310, 600/340, 407, 473, 476; 356/432
See application file for complete search history.

(56) References Cited

U.S. PATENT DOCUMENTS

| 6,078,829 | A  | * | 6/2000 | Uchida et al. | 600/310 |
| 6,080,110 | A  |   | 6/2000 | Thorgersen | 600/500 |
| 6,115,621 | A  | * | 9/2000 | Chin | 600/323 |
| 6,128,091 | A  | * | 10/2000 | Uchida et al. | 356/432 |
| 7,209,775 | B2 |   | 4/2007 | Bae et al. | 600/340 |
| 2007/0008738 | A1 | * | 1/2007 | Han et al. | 362/607 |

FOREIGN PATENT DOCUMENTS

| KR | 2007-0092869 | 9/2007 |
| KR | 2008-0047902 | 5/2008 |

* cited by examiner

*Primary Examiner* — Tse Chen
*Assistant Examiner* — Jason Ip
(74) *Attorney, Agent, or Firm* — Cha & Reiter, LLC

(57) ABSTRACT

A sensor for measuring living body information includes a light guide member for guiding a first light; a light extracting member, disposed adjacent to the light guide member, for outputting the first light guided by the light guide member to an exterior of the light guide member through contact with the light guide member; and a light coupling member, disposed adjacent to the light guide member, for coupling a second light to the light guide member through contact with the light guide member.

8 Claims, 8 Drawing Sheets

SENSOR FOR MEASURING LIVING BODY INFORMATION AND EARPHONE HAVING THE SAME

CLAIM OF PRIORITY

This application claims the benefit under 35 U.S.C. §119 (a) of a Korean Patent Application filed in the Korean Intellectual Property Office on Aug. 27, 2007 and assigned Serial No. 2007-86098, the disclosures of which are incorporated herein by reference.

BACKGROUND OF THE INVENTION

1. Field of the Invention

The present invention relates generally to a sensor for detecting a user's physiologic information, and in particular, to a compact sensor for measuring the physiologic data, such as a pulse rate.

2. Description of the Related Art

The pulse rate is a numerical value based on which the stress, the state of exercise, the quantity of exercise, etc. can be measured. Conventionally, an electrocardiogram (ECG) sensor has been deployed to measure the pulse rate by detecting ECG signals using multipolar electrodes. In addition, a photosensor, by irradiating a light on a skin surface of a living body using a light emitting diode (LED), detects a light output from the skin surface within the living body using a photodiode (PD).

Recently, intensive research efforts are being concentrated on small devices equipped with a sensor for measuring a user's physical information. However, since the above-stated ECG sensor and photosensor require a dedicated space for their installation, they can be hardly applied to the small devices.

Therefore, there is a need a compact sensor for measuring living body information that can be readily incorporated and utilized in small devices such as an earphone.

SUMMARY OF THE INVENTION

An aspect of the present invention is to address at least the problems and/or disadvantages and to provide at least the advantages described below. Accordingly, an aspect of the present invention is to provide a sensor for measuring a person's physiologic information, which is suitable to be applied on small devices for operation.

According to another aspect of the present invention, a sensor for measuring living body information includes: a light guide member for guiding a first light; a light extracting member, disposed adjacent to the light guide member, for outputting the first light guided by the light guide member to an exterior of the light guide member through contact with the light guide member; and a light coupling member, disposed adjacent to the light guide member, for coupling a second light to the light guide member through contact with the light guide member.

According to another aspect of the present invention, an earphone includes: a speaker for outputting a sound wave; an optical circuit, disposed outside the speaker, for generating and outputting a first light, and outputting a living body signal obtained by photoelectrically converting an input second light; and a sensor strip, disposed outside the optical circuit, for outputting the first light input from the optical circuit to an exterior of the earphone, and outputting the second light input from the exterior of the earphone to the optical circuit.

BRIEF DESCRIPTION OF THE DRAWINGS

The above and other aspects, features and advantages of the present invention will become more apparent from the following detailed description when taken in conjunction with the accompanying drawings in which.

DETAILED DESCRIPTION OF THE INVENTION

Now, embodiments of the present invention will now be described in detail with reference to the annexed drawings. In the following description, a detailed description of known functions and configurations incorporated herein has been omitted for clarity and conciseness.

Figure 1:
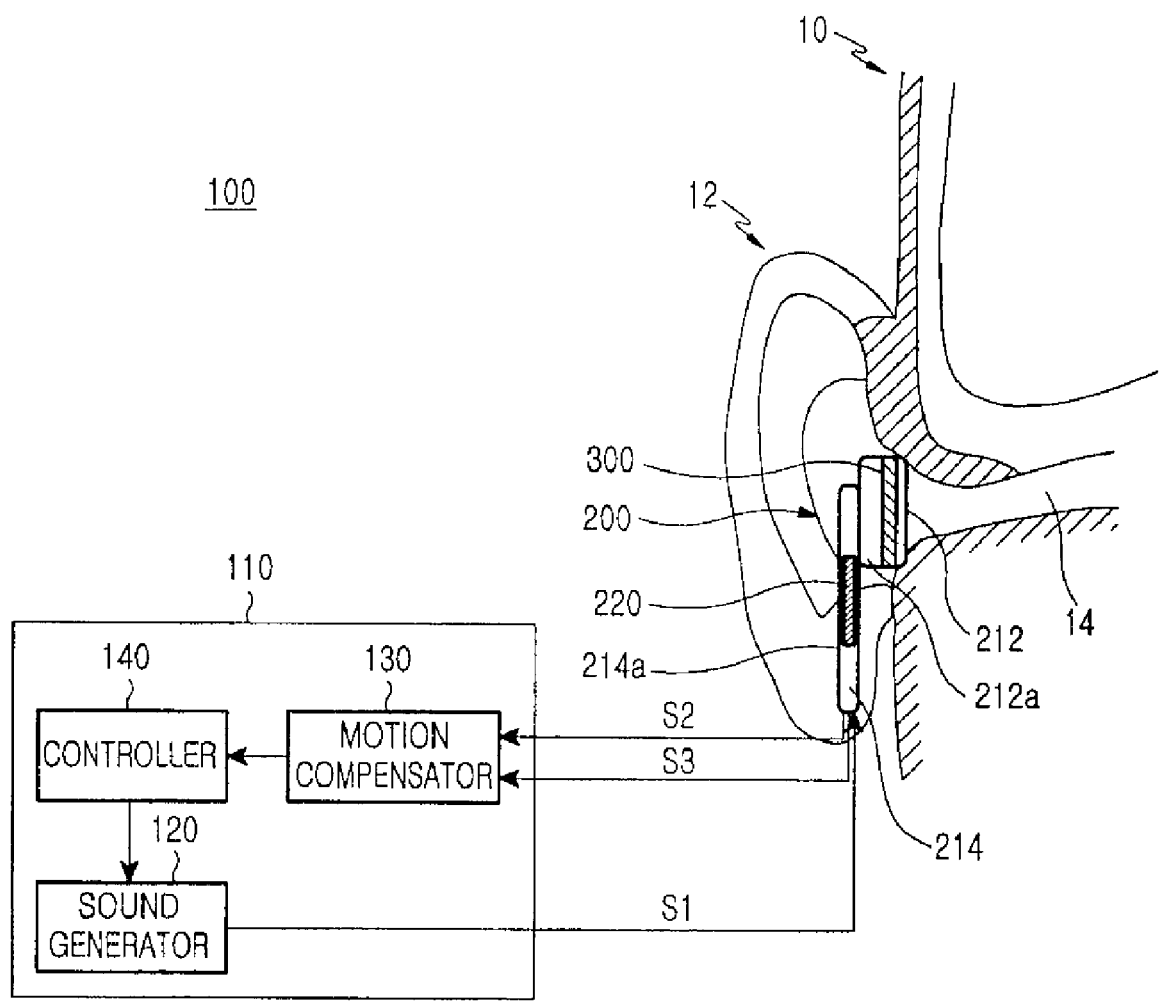
FIG. 1 is a diagram illustrating a living body information measuring system according to an embodiment of the present invention.
Figure 2:
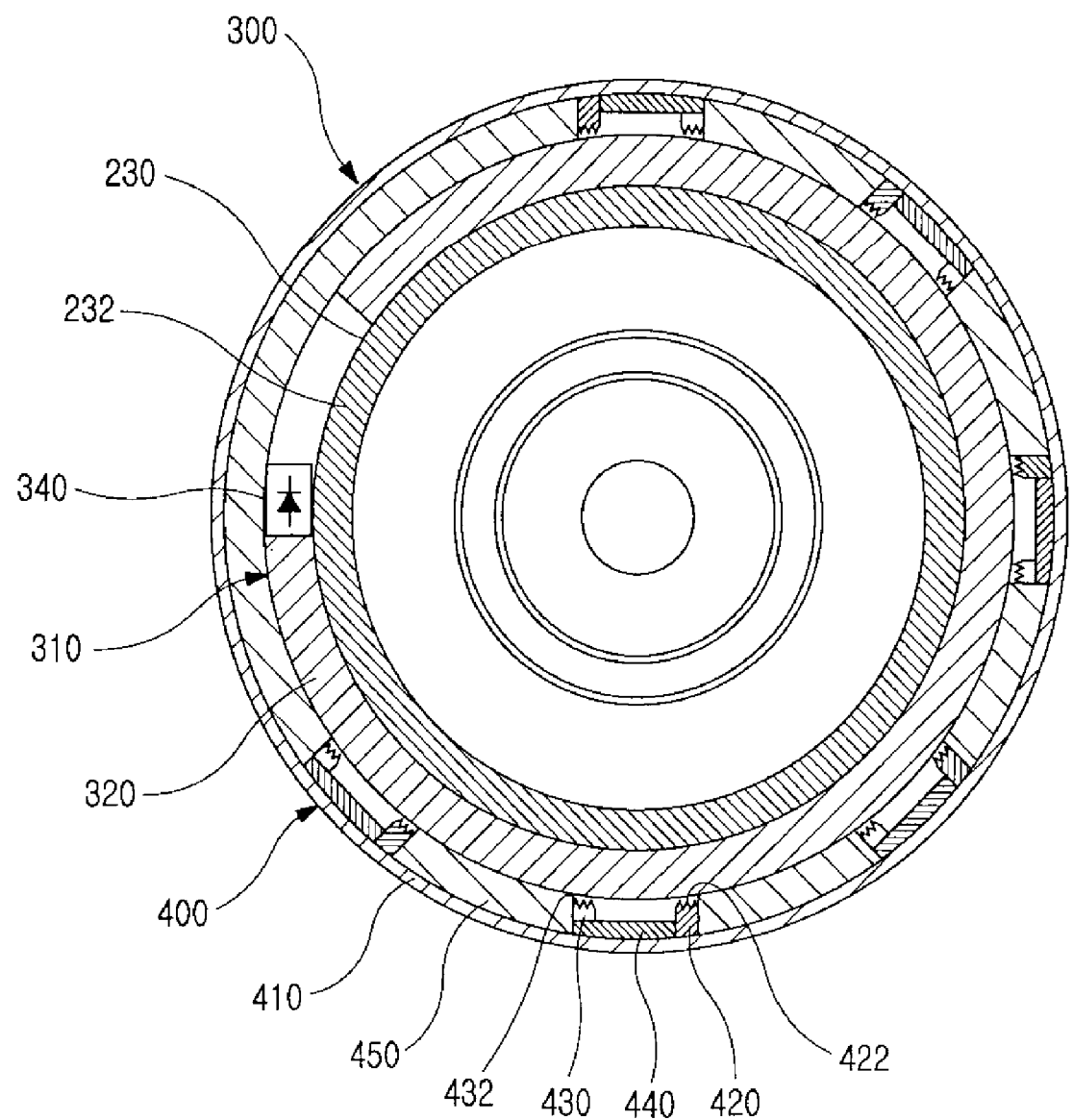
FIG. 2 is a front cross-sectional view illustrating the earphone shown in FIG. 1.

FIG. 1 is a diagram illustrating a measuring system according to an embodiment of the present invention, and FIG. 2 is a front cross-sectional view illustrating the earphone system shown in FIG. 1. As shown in FIGS. 1 and 2, the measuring system 100 includes an earphone 200 for outputting sounds and measuring physiologic information, and a sound device 110 for generating sound signals and calculating the physiologic information.

The earphone 200, which is adoptively inserted and fixed into an ear canal 14 of an ear 12 of a user 10, includes housings 212 and 214, a speaker 230, a living body information measuring sensor 300, and an accelerometer 220.

The housings 212 and 214 include a hemispherical body part 212a for accommodating the speaker 230 and the living body information measuring sensor 300, and a connecting part 214a which extends long in a cylindrical shape so that it communicates with the body part 212a, and which accommodates the accelerometer 220. An earphone cable (not shown) is connected to the body part 212a via the connecting part 214a and connects the sound device 110 to the earphone 200. The earphone cable further includes conductive lines for delivering a sound signal S1, a living body signal S2, and a motion signal S3.

The speaker 230 is accommodated in the body part 212, and serves to convert an input sound signal S1 into a sound wave.

The accelerometer 220, which is accommodated in the connecting part 214, is used for removing noises occurring due to a motion of the user 10. The accelerometer 220 also outputs a motion signal S3 generated according to the motion of the user 10.

The living body information measuring sensor 300, which is accommodated in the body part 212, irradiates a first light on an inner-ear skin of the user 10, generates a living body signal S2 obtained by photoelectrically converting a second light being output from the inner-ear skin of the user 10, and then outputs the living body signal S2. The 'second light' refers to a light being output from the inner-ear skin due to its scattering within the inner-ear skin, from among the first lights irradiated on the inner-ear skin.

The sound device 110 includes a sound generator 120, a motion compensator 130, and a controller 140.

The sound generator 120, under the control of the controller 140, generates a sound signal S1, and outputs the generated sound signal S1 to the earphone 200.

The motion compensator 130 receives a motion signal S3 and a living body signal S2 from the earphone 200, removes noises caused by a motion of the user 10, included in the living body signal S2, based on the motion signal S3, thereby generating a compensated living body signal, and outputs the compensated living body signal to the controller 140.

The controller 140 calculates a pulse rate of the user 10 from a periodic power change of the compensated living body signal received from the motion compensator 130. Note that motion compensation and pulse rate calculation are readily known by those skilled in this art, thus a detailed description thereof is omitted herein.

The living body information measuring sensor 300 includes an optical circuit and a sensor strip.

Figure 3A:
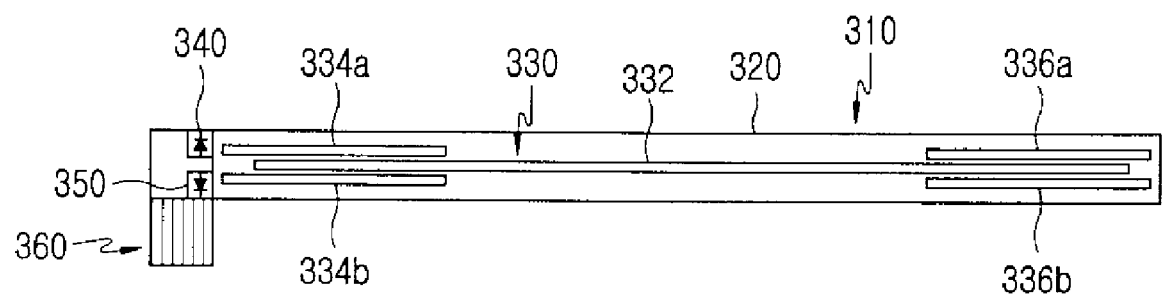
FIGS. 3A and 3B are diagrams illustrating the optical circuit shown in FIG. 2.
Figure 3B:
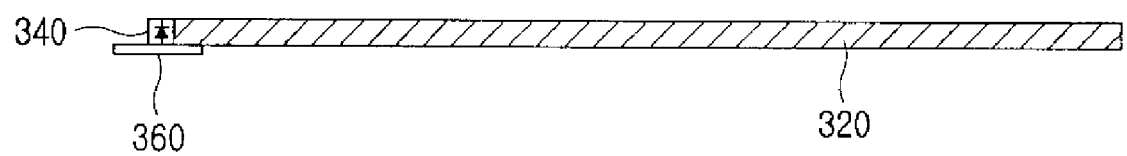

FIGS. 3A and 3B are diagrams illustrating the optical circuit. Specifically, FIG. 3A is a plane view illustrating the optical circuit, and FIG. 3B is a side view illustrating the optical circuit.

The optical circuit 310, which is disposed around a frame 232 of the speaker 230, generates and outputs a first light, and generates a living body signal S2 by photoelectrically converting a second light responsive to the first light.

The optical circuit 310 includes a light guide member 320 for guiding a light, a light source 340 for generating a light, an optical detector 350 for photoelectric conversion, and a flexible printed circuit board 360 for driving the light source 340 and the optical detector 350. The expression 'guiding a light' as used herein represents that the light progresses through the total internal reflection between the top surface and the bottom surface of the light guide member 320.

The light source 340 outputs a first light having a near infra-red (NIR) wavelength, and the wavelength can be, for example, about 940 nm. A LED, a laser diode (LD), etc. can be used as the light source 340.

The light guide member 320 generally has a shape of a rectangular plate, and has a top surface, a bottom surface, and four side surfaces. The first light coupled to an interior of the light guide member 320 is guided from a first side surface of the light guide member 320 to a second side surface situated in the opposite side thereof through the total internal reflection between the top surface and the bottom surface. In this case, the first side surface of the light guide member 320 faces a light emitting surface of the light source 340, and the first light output from the light source 340 is coupled to the interior of the light guide member 320 through the first side surface. The light guide member 320, as it has an elasticity (in other words, self-restoring force), is restored to its original shape after being distorted by the external pressure. The light guide member 320 can be formed of a material having low hardness, high elastic strain, high elastic recovery force, and high optical transmittance. The light guide member 320 may be formed of a material such as polycarbonate, acrylic resin, polyurethane, polymethylmethacrylate (PMMA), silicone, etc.

The light guide member 320 includes a light blocking member 330 which is formed so that its longitudinal extension line is situated between the light source 340 and the optical detector 350.

The light blocking member 330 is situated in the center of the light guide member 320, and on the basis of the light blocking member 330, the light guide member 320 is divided into a light output part toward the light source 340 and a light input part toward the optical detector 350. The light blocking member 330 blocks the light such that a light being incident from any one side cannot progress to another side passing through the light blocking member 330. The light blocking member 330 extends long in a longitudinal direction (i.e., a direction of the shortest moving distance reaching from the first side surface to the second side surface) of the light guide member 320, and includes at least one hole that passes through the light guide member 320 in a thickness direction (i.e., a direction of the shortest moving distance from the bottom surface to the top surface).

In this embodiment, the light blocking member 330 includes a first hole 332 having the longest length, second and third holes 334a and 334b adjacently disposed at both sides of one end of the first hole 332, and fourth and fifth holes 336a and 336b adjacently disposed at both sides of another end of the first hole 332. The second and third holes 334a and 334b are situated closer to the second side surface compared with the first hole 332, and the fourth and fifth holes 336a and 336b are situated closer to the first side surface compared with the first hole 332. Both ends of each hole, as they have a rounded shape, allow a light reflected on each end to be output to the exterior passing through the side surfaces of the light guide member 320. Optionally, a reflection layer having a high reflectance (e.g., 90-100%) can be stacked on a corresponding inner surface of the light guide member 320, which defines each hole.

The optical detector 350 is disposed such that its light receiving surface faces the first side surface of the light guide member 320, and photoelectrically converts the second light being incident thereupon after penetrating the first side surface of the light guide member 320, thereby generating a living body signal. A photodiode, a phototransistor, etc. can be used as the optical detector 350.

The flexible printed circuit board 360 is attached to an end of the bottom surface toward the first side surface of the light guide member 320. The light source 340 is mounted on the top surface of the flexible printed circuit board 360 so that the first side surface and the light emitting surface of the light guide member 320 face each other, and the optical detector 350 is mounted on the top surface of the flexible printed circuit board 360 so that the first side surface and the light receiving surface of the light guide member 320 face each other. The flexible printed circuit board 360 provides a driving voltage to the light source 340 and the optical detector 350, and delivers the living body signal S2 output from the optical detector 350 to the sound device 110.

The sensor strip 400, which is disposed around the optical circuit 310, outputs the first light being guided by the light guide member 320 to an inner-ear skin through contact with the light guide member 320, and couples the second light being output from the inner-ear skin to the light guide member 320 through the contact with the light guide member 320.

Figure 4A:
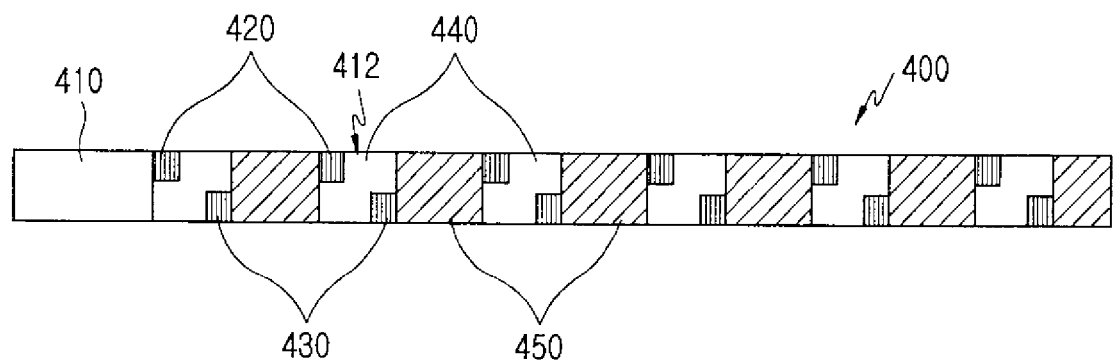
FIGS. 4A and 4B are diagrams illustrating the sensor strip shown in FIG. 2.
Figure 4B:
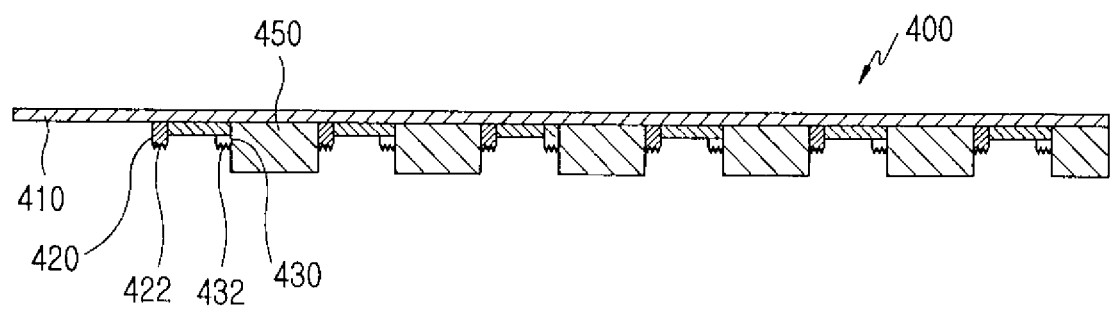

FIGS. 4A and 4B are diagrams illustrating the sensor strip 400. The sensor strip 400 includes a base part 410 having a shape of a rectangular strip, a plurality of light extracting/coupling units 412, and a plurality of spacers 450. The light extracting/coupling units 412 each includes a light extracting member 420, a light coupling member 430, and a fixing member 440. The light extracting/coupling units 412 and the spacers 450 are attached to the base part 410 so that they are alternately disposed along the longitudinal direction of the base part 410. The base part 410 is formed of a material through which the first and second lights can penetrate.

The fixing member(s) 440 has a shape of a square block, and the light extracting member(s) 420 and the light coupling member(s) 430 are disposed at two facing corners of the fixing member 440, respectively. A distance between the light extracting member 420 and the light coupling member 430 along the width direction of the base part 410 is set to be greater than at least the width of the first hole 332 of the light blocking member 330, and is preferably set to be greater than the total width of the light blocking member 330. Such setting is to ensure that the light extracting member 420 contacts the light output part, and the light coupling member 430 contacts the light input part. The fixing member 440 is formed of a material capable of absorbing the first and second lights.

The light extracting member 420 and the light coupling member 430 have the substantially same thickness, and the thickness is set to be greater than a thickness of the fixing member 440. That is, the light extracting member 420 and the light coupling member 430 are adapted to protrude over the top surface of the fixing member 440. The light extracting member 420 outputs the first light being guided by the light guide member 320 to the inner-ear skin through the contact with the light guide member 320. The light coupling member 430 couples the second light being output from the inner-ear skin to the light guide member 320 through the contact with the light guide member 320. The light extracting member 420 and the light coupling member 430 have a refraction index capable of minimizing the light coupling loss caused by reflection while breaking the total reflection condition of the light progressing into the light guide member 320 upon contact with the light guide member 320, i.e., has a refraction index which is equal or similar to a refraction index of the light guide member 320, and can be formed of the same material as that of the light guide member 320.

The spacers 450 have a greater thickness than that of the light extracting member 420 and the light coupling member 430, and are formed of a material capable of extending/retracting along their thickness directions and of absorbing the first and second lights.

Figure 5:
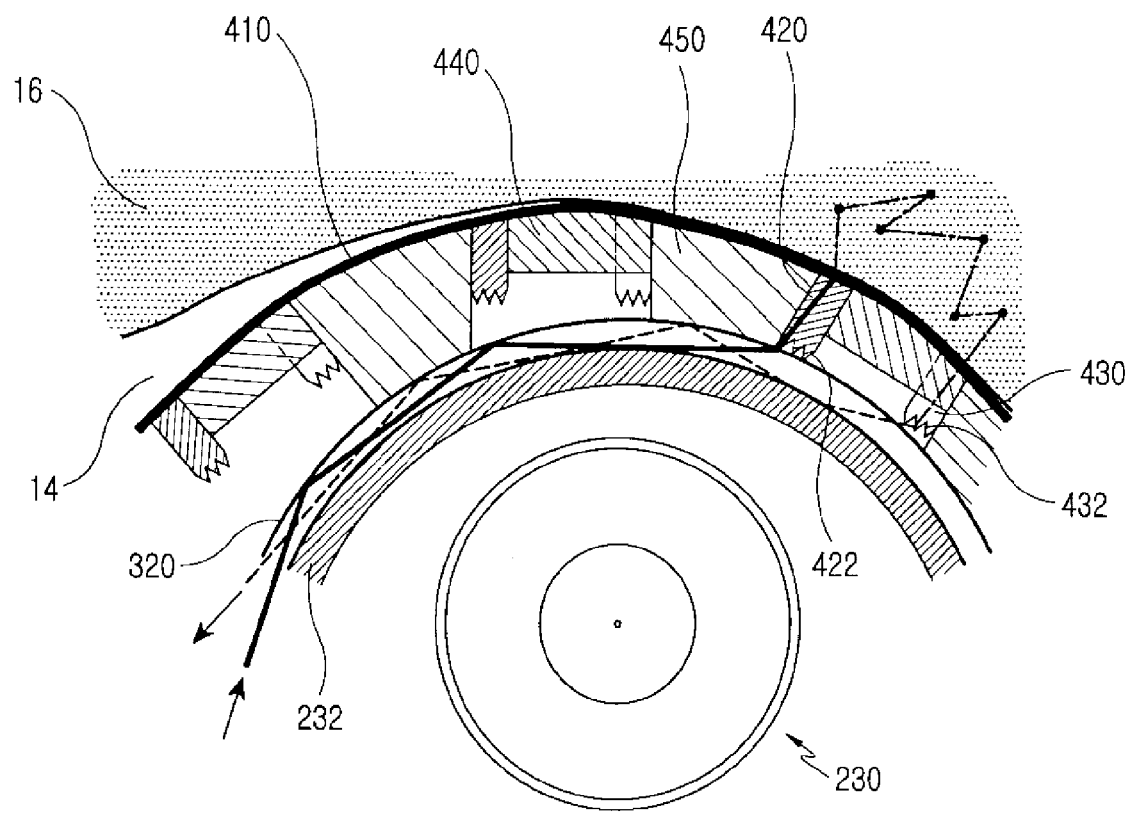
FIG. 5 is a diagram illustrating an operation of the living body information measuring sensor shown in FIG. 2.

FIG. 5 is a diagram illustrating an operation of the living body information measuring sensor 300.

A first light output from the light source 340 undergoes total-reflection progress into the light guide member 320 after being coupled to the light guide member 320. In the process where the earphone 200 is inserted and fixed into the ear canal 14 of the user 10, at least a part of the sensor strip 400 is pressed while making pressure contact with the inner-ear skin 16. As the spacers 450 belonging to the pressed part of the sensor strip 400 are pressed up to the thickness of the corresponding light extracting member 420 and light coupling member 430 situated between the spacers 450, the light extracting member 420 and the light coupling member 430 mace a contact with the top surface of the light guide member 320. In the boundary between the light guide member 320 and the light extracting member 420, where they contact each other, since the total reflection condition of the first light cannot be satisfied, the first light incident upon the top surface of the light extracting member 420 penetrates the top surface of the light extracting member 420 without suffering almost any loss. Thereafter, the first light that penetrated the top surface of the light extracting member 420 is incident upon the inner-ear skin 16 after penetrating the base part 410.

The light, i.e., second light, being output from the inner-ear skin 16 due to its scattering within the inner-ear skin 16, from among the first lights incident upon the inner-ear skin 16, is incident upon the light coupling member 430 after penetrating the base part 410. In the boundary between the light guide member 320 and the light extracting member 420, where they contact each other, since the second light can penetrate the top surfaces of the light coupling member 430 and the light guide member 320 without almost any loss, the second light is coupled to the light guide member 320. Thereafter, as the second light coupled to the light guide member 320 is guided by the light guide member 320, it is incident upon the optical detector 350, and the optical detector 350 generates a living body signal S2 by photoelectrically converting the second light incident thereupon.

In order to increase the light coupling efficiency, it is preferable to deflect the first light, which was incident to be inclined against the thickness direction of the light extracting member 420, in the thickness direction of the light extracting member 420, and to deflect the second light, which was incident in the thickness direction of the light coupling member 430, to be inclined at an angle satisfying the total reflection condition within the light guide member 320. To this end, the light extracting member 420 and the light coupling member 430 each can include a pattern 422 (432) for changing a path of the light incident upon their top surfaces, and each of the patterns can be composed of a plurality of protrusions whose ends have a wedge shape.

Figures 6A, 6B:
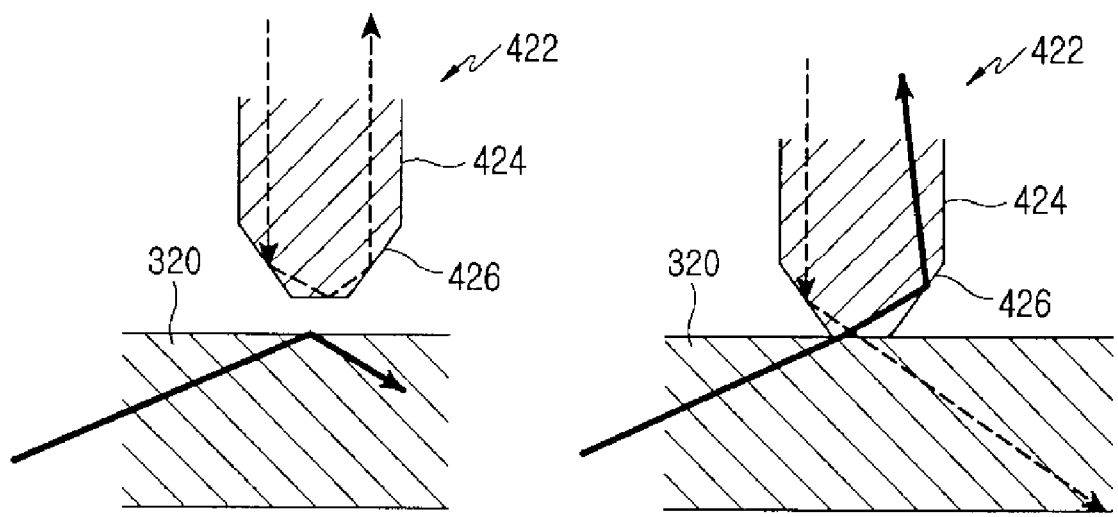
FIGS. 6A and 6B are diagrams illustrating a part of the pattern included in the light extracting member shown in FIG. 2.

FIGS. 6A and 6B are diagrams illustrating a part of the pattern 422 included in the light extracting member 420. Specifically, FIG. 6A illustrates a case where the light extracting member 420 is spaced apart from the light guide member 320, and FIG. 6B illustrates a case where the light extracting member 420 contacts the light guide member 320.

Referring to FIG. 6A, there is shown one protrusion 424 constituting the pattern 422, and since the light guide member 320 is spaced apart from the light extracting member 420, no light coupling occurs between the light guide member 320 and the light extracting member 420.

Referring to FIG. 6B, the first light progressing into the light guide member 320 is incident upon the protrusion 424 to be inclined, and deflected in the thickness direction of the light extracting member 420 after being reflected by an inclined surface 426 at an end of the protrusion 424. In addition, the second light incident upon the protrusion 424 is coupled to the light guide member 320 after being reflected by the inclined surface 426 at an end of the protrusion 424, and is guided by the light guide member 320.

Figure 7A:
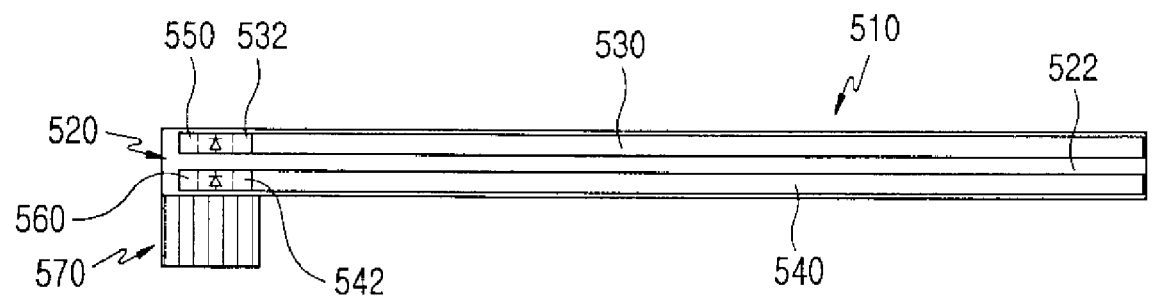
FIGS. 7A and 7B are diagrams illustrating an optical circuit according to another embodiment of the present invention.
Figure 7B:
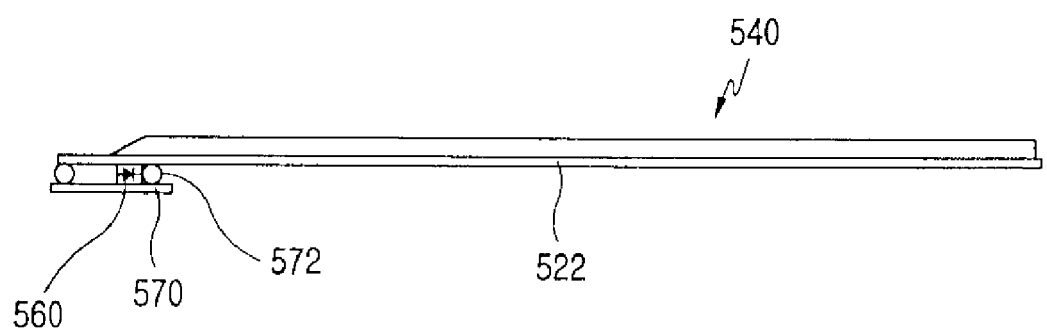

FIGS. 7A and 7B are diagrams illustrating an optical circuit according to another embodiment of the present invention. Specifically, FIG. 7A is a plane view illustrating the optical circuit, and FIG. 7B is a side view illustrating the optical circuit.

As shown, the optical circuit 510 includes a light guide member 520 for guiding a light, a light source 550 for generating a light, an optical detector 560 for photoelectric conversion, and a flexible printed circuit board 570 for driving the light source 550 and the optical detector 560.

The light guide member 520 includes a flexible substrate 522, and a light output part 530 and a light input part 540, both of which are stacked on the substrate 522 such that they are disposed in parallel to be spaced apart from each other. The light output part 530 and the light input part 540 each generally have a shape of a rectangular strip, and have a top surface, a bottom surface and four side surfaces.

The first light coupled to an interior of the light output part 530 is guided from the first side surface 532 of the light output part 530 to the second side surface situated in the opposite side thereof through the total internal reflection between the top surface and the bottom surface. In this case, the first side surface 532 of the light output part 530 is inclined 45° against each of its longitudinal direction and the light output direction (i.e., a normal line of the light emitting surface) of the light source 550. The first light output from the light source 550 is incident upon the first side surface through the substrate 522, and the first light reflected by the first side surface 532 undergoes total-reflection progress into the light output part 530.

The second light coupled to the light input part 540 is guided to the first side surface 542 of the light input part 540 through the total internal reflection between the top surface and the bottom surface. In this case, the first side surface 542 of the light input part 540 is inclined 45° against each of its longitudinal direction and the normal line of the light receiving surface of the optical detector 560. The second light reflected after being incident upon the first side surface 542 is incident upon the optical detector 560 after penetrating the substrate 522.

The light source 550 outputs the first light having a NIR wavelength.

The optical detector 560 generates a living body signal by photoelectrically converting the second light incident thereupon.

The flexible printed circuit board 570 is attached to an end of the bottom surface of the substrate 522 with a flip-chip technique based on a solder ball 572. The light source 550 is mounted on the printed circuit board 570 so that its light emitting surface faces the first side surface 532 of the light output part 530, and the optical detector 560 is mounted on the printed circuit board 570 so that its light receiving surface faces the first side surface 542 of the light input part 540. The printed circuit board 570 provides a driving voltage to the light source 550 and the optical detector 560, and delivers the living body signal output from the optical detector 560 to the sound device shown in FIG. 1.

Figure 8A:
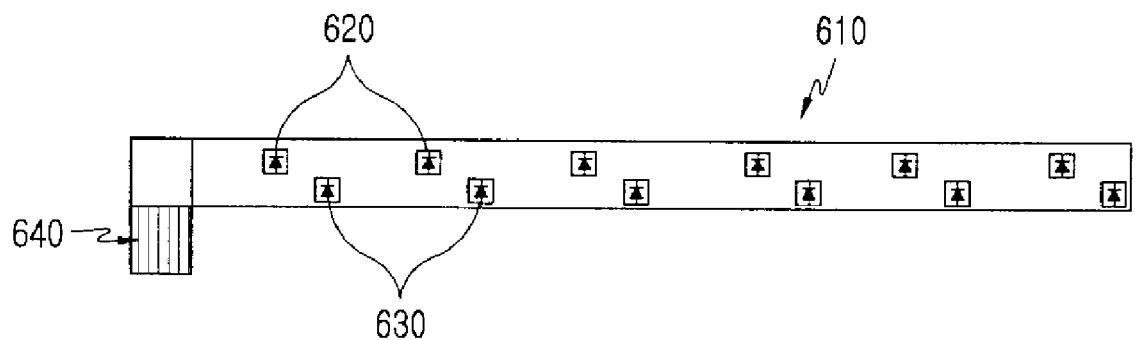
FIGS. 8A and 8B are diagrams illustrating an optical circuit according to yet another embodiment of the present invention.
Figure 8B:
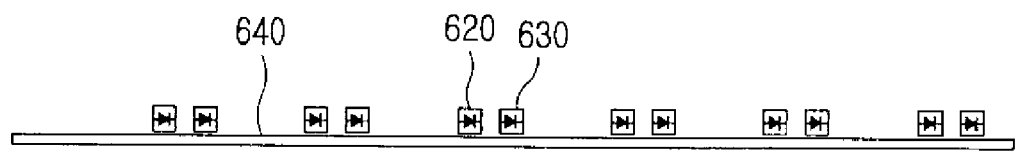

FIGS. 8A and 8B are diagrams illustrating an optical circuit according to yet another embodiment of the present invention. Specifically, FIG. 8A is a plane view illustrating the optical circuit, and FIG. 8B is a side view illustrating the optical circuit.

As shown, the optical circuit 610 includes a plurality of light sources 620 for generating a light, a plurality of optical detectors 630 for photoelectric conversion, and a flexible printed circuit board 640 for driving the light sources 620 and the optical detectors 630

The light sources 620 are mounted on the printed circuit board 640 so that they are mapped to the light extracting members 420 of the sensor strip 400 shown in FIGS. 4A and 4B on a one-to-one basis, and the light sources 620 each output a first light having a NIR wavelength.

The optical detectors 630 are mounted on the printed circuit board 640 so that they are mapped to the light coupling members 430 of the sensor strip 400 shown in FIGS. 4A and 4B on a one-to-one basis, and the optical detectors 630 each convert the second light incident thereupon into an electrical signal.

The flexible printed circuit board 640 provides a driving voltage to the light sources 620 and the optical detectors 630, and delivers the living body signal output from the optical detectors 630 to the sound device 110 shown in FIG. 1.

As is apparent from the foregoing description, the sensor for measuring living body information according to the present invention is provided in the strip shape which is small in thickness and size, so it is suitable to be applied to small devices such as an earphone. When applied to the earphone, the sensor for measuring living body information is disposed such that it is wound outside the speaker, making it possible to excellently provide the music listening function without almost any modification of the external design of the earphone.

While the invention has been shown and described with reference to a certain preferred embodiment thereof, it will be understood by those skilled in the art that various changes in form and details may be made therein without departing from the spirit and scope of the invention as defined by the appended claims.

For example, the optical circuit 310 shown in FIGS. 3A and 3B can further include first and second polariscopes, and the first and second polariscopes can perform a function of preventing the first light output from the light source 340 from being directly input to the optical detector 350. The first polariscope is disposed between the first side surface of the light guide member 320 and the light emitting surface of the light source 340, and the second polariscope is disposed between the first side surface of the light guide member 320 and the light receiving surface of the optical detector 350. A first polarization axis of the first polariscope is perpendicular to a second polarization axis of the second polariscope. The first light output from the light source 340 is polarized along the first polarization axis as it passes through the first polariscope. When the polarized first light is incident upon the second polariscope, since the polarization direction of the first light is perpendicular to the second polarization axis of the second polariscope, the first light is blocked by the second polariscope.

What is claimed is:

1. An earphone comprising:
a speaker for outputting a sound wave;
an optical circuit having a light source, disposed circumferentially around the speaker, configured to generate and output a first light, the first light being output towards a living body to produce a second light reflected from the living body, the optical circuit generating a living body signal that is obtained by detecting and photoelectrically converting the second light into an electric signal, and the optical circuit further having a light guide member for guiding the first and second lights; and
a sensor strip, disposed circumferentially around the optical circuit, configured to output the first light from the optical circuit towards the living body, and outputting the second light reflected from the living body to the optical circuit;
wherein the sensor strip includes at least one light extracting member and at least one light coupling member, each disposed alongside the light guide member, the light extracting member outputting the first light from the light guide member through contact with the light guide member and the light coupling member coupling the second light to the light guide member through contact with the light guide member.

2. The earphone of claim 1, wherein the optical circuit further comprises a printed circuit board, coupled to the light guide member, for providing a driving voltage to the light source and an optical detector.

3. The earphone of claim 1, wherein the light guide member further comprises:
a substrate;
a light output part stacked on the substrate for receiving the first light from the light source; and a light input part stacked on the substrate and spaced apart from the light output part for outputting the second light to an optical detector.

4. The earphone of claim 1, wherein the optical circuit comprises:
   a plurality of light sources for generating the first light;
   a plurality of optical detectors for outputting the living body signal obtained by photoelectrically converting the second light; and
   a printed circuit board for providing a driving voltage to the light sources and the optical detectors, with the light sources and the optical detectors disposed alternately on a top surface thereof along its circumferential direction.

5. The earphone of claim 1, wherein the at least one light extracting member comprises a plurality of light extracting members, and the at least one light coupling member comprises a plurality of light coupling members, the sensor strip comprising a plurality of light extracting/coupling units distributed around the light guide member, each comprising one of the light extracting members and one of the light coupling members.

6. The earphone of claim 5, wherein the sensor strip further comprises a plurality of spacers separating the light extracting units from one another, the spacers being compressible and having a greater width than the light extracting members and the light coupling members when in an uncompressed state, whereby when the earphone is placed within a user's ear, at least one spacer is compressed to cause the contact of the at least one light extracting unit and the at least one light coupling unit with the light guide member.

7. The earphone of claim 6, wherein the sensor strip further comprises:
   a plurality of fixing members, situated between the spacers, for fixing in place pairs of light exreacting members and light coupling members; and
   a base part to which the light extracting member, the light coupling member, the spacers and the fixing member are attached.

8. The earphone of claim 1, wherein the light guide member guides the first and second lights through total internal reflection between a top surface and a bottom surface of the light guide member, the top surface contacting the sensor strip and the bottom surface contacting the speaker.

* * * * *